United States Patent
Majima et al.

(10) Patent No.: US 6,350,585 B1
(45) Date of Patent: *Feb. 26, 2002

(54) REAGENT FOR ASSAY OF AMYLASE ISOZYME ACTIVITY

(75) Inventors: Keiichi Majima, Tsuruga; Shigeki Asano, Tokyo; Yoshihisa Kawamura, Tsuruga, all of (JP)

(73) Assignee: Toyo Boseki Kabushiki Kaisha, Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/253,020

(22) Filed: Feb. 19, 1999

(30) Foreign Application Priority Data

Feb. 19, 1998 (JP) .............................. 10-037583
Feb. 1, 1999 (JP) .............................. 11-023804

(51) Int. Cl.⁷ .................. C12Q 1/40; G01N 33/573; C12N 9/26; C07K 16/40; C07H 3/04
(52) U.S. Cl. .............. 435/22; 435/7.4; 435/201; 530/388.26; 536/123.1; 536/123.13
(58) Field of Search ................. 435/22, 7.4, 201; 536/123.1, 123.13; 423/366, 410, 22, 7.4, 201; 530/388.26

(56) References Cited

U.S. PATENT DOCUMENTS

| | | | |
|---|---|---|---|
| 4,622,295 A | 11/1986 | Ikenaka et al. ............... 435/22 |
| 4,697,006 A | 9/1987 | Ikenaka et al. ............. 536/17.2 |
| 4,945,043 A * | 7/1990 | Gerber ........................... 435/7 |
| 4,952,507 A * | 8/1990 | Woodward ............. 435/240.27 |
| 5,194,382 A | 3/1993 | Herrmann et al. .......... 435/207 |
| 5,254,677 A | 10/1993 | Guder et al. ................. 435/7.9 |
| 5,314,803 A * | 5/1994 | Wilk et al. .................... 435/7.4 |
| 5,319,076 A | 6/1994 | Hasegawa et al. ............ 536/4.1 |
| 5,378,831 A | 1/1995 | Usui et al. ................ 536/123.1 |
| 5,393,660 A * | 2/1995 | Kitahata et al. ............... 435/22 |
| 5,573,918 A | 11/1996 | Lenz et al. .................. 435/7.4 |

FOREIGN PATENT DOCUMENTS

| | | | |
|---|---|---|---|
| EP | 0 222 923 | 5/1987 | ......... A61K/39/395 |
| JP | 61-209600 | 9/1986 | |
| JP | 63-183595 | 7/1988 | |
| JP | 1-98498 | 4/1989 | |
| JP | 4-37380 | 6/1992 | |
| JP | 4-193892 | 7/1992 | |
| JP | 4-52279 | 8/1992 | |
| JP | 4-229196 | 8/1992 | |

OTHER PUBLICATIONS

Lehninger, "Biochemistry", The Johns Hopkins University School of Medicine (1981) chapter 8 pp. 181–213.*

Gella et al.; "Determination of Total and Pancreatic X–Amylase in Human Serum With 2–Chloro–4–Nitrophenyl–X–D–Maltotrioside As Substrate"; Clinica Chimica Acta; No. 259; 1997; pp. 147–160.

Winn–Deen et al.; "Development of A Direct Assay for A X–Amylase"; Clin. Chem.; vol. 34, No. 10; 1998; pp. 2005–2008.

* cited by examiner

Primary Examiner—Michael P. Woodward
Assistant Examiner—Marjorie A. Moran
(74) Attorney, Agent, or Firm—Foley & Lardner (57) ABSTRACT

A reagent for amylase isozyme activity assay, which contains 2-chloro-4-nitrophenyl 4-O-β-D-galactopyranosylmaltoside, an antibody inhibiting S-type amylase activity or P-type amylase activity, and an amylase activator, and methods for assaying amylase isozyme activity using the regent is provided. According to the present invention, amylase isozyme activity can be accurately and easily assayed using a low concentration activator and an antibody having S-type amylase or P-type amylase activity inhibitory action without using an adjuvant enzyme.

12 Claims, 6 Drawing Sheets

REAGENT FOR ASSAY OF AMYLASE ISOZYME ACTIVITY

TECHNICAL FIELD OF THE INVENTION

The present invention relates to a novel reagent for the assay of amylase isozyme activity and assay methods using the reagent. More particularly, the present invention relates to a novel reagent for simple assay of amylase isozyme activity, comprising an antibody which inhibits S-type amylase activity or P-type amylase activity but not containing an adjuvant enzyme and assay methods using the reagent.

BACKGROUND OF THE INVENTION

α-Amylase contained in a body fluid, such as pancreatic juice, urine and the like, is mainly classified into two kinds of isozymes of P-type amylase mostly derived from pancreas and S-type amylase mostly derived from salivary gland. Various diseases are diagnosed by assaying these isozymes. Of these, P-type amylase is said to be useful as a marker of acute pancreatitis, since it has high organ specificity.

Conventionally, an electrophoretic method and a method using a wheat-derived amylase activity inhibitor have been used for amylase isozyme assay. These methods, nevertheless, are defective in that the operation is complicated and time-consuming, P-type amylase activity cannot be assayed directly, and so on. For example, a method using a wheat-derived amylase inhibitor is known, but the isozyme selectivity of the inhibitor is insufficient in this method. As a result, P-type amylase activity cannot be assayed directly so that complicated quantitative calculation becomes necessary, such as depicting a calibration curve and the like. Although an electrophoretic method was known long before that, this method requires complicated operation and skillful interpretation of the results, which have been pointed out as defects.

Meanwhile, various methods utilizing different reactivities of isozymes to a certain substrate or two kinds of substrates having different structures have been disclosed (Japanese Patent Examined Publication No. 24998/1992; Japanese Patent Unexamined Publication No. 98498/1989; Japanese Patent Unexamined Publication No. 193892/1992; Japanese Patent Unexamined Publication No. 229196/1992; Japanese Patent Examined Publication No.52279/1992; and the like). These methods again require complicated reactions that prevent direct assay of P-type amylase activity and necessitate complicated quantitative calculation involving depicting a calibration curve and the like.

A method using ferric ion as an inhibitor has been also disclosed (Japanese Patent Unexamined Publication No. 209600/1986). This method similarly requires complicated quantitative calculation.

In recent years, methods using a monoclonal antibody having a higher isozyme selectivity have been disclosed. A method using an anti-P-type isozyme monoclonal antibody is known Japanese Patent Examined Publication No. 46116/1991), but this method has a defect in that the manipulation is complicated due to an additional step for separating an antigen-antibody complex from others.

In addition, a method is known wherein one or several kinds of monoclonal antibodies is/are used to specifically inhibit S-type isozyme alone, whereby P-type isozyme activity is specifically assayed (Japanese Patent Examined Publication No. 37380/1992 and Japanese Patent Examined Publication No. 2600/1988).

While the substrates for amylase assay to be used for these methods are not particularly limited, it does not necessarily mean that any substrate for amylase assay can be used for these methods. Moreover, since the substrate for amylase activity assay to be combined has superiority or inferiority in performance, which reagent to select is practically critical The reagent for α-amylase activity assay to be combined with the method using the above-mentioned antibody is often a reagent for general use for an automatic analyzer. Of such reagents, reagents containing various maltooligosaccharides or derivatives thereof as substrate are typically used. For example, (1) maltooligosaccharide having glucose units of 4–7, (2) a derivative (glucose units 4–7) wherein aglycon, which becomes optically assayable upon liberation, has been bound with the reducing terminal of maltooligosaccharide, (3) a derivative (glucose units 4–7) wherein aglycon, which becomes optically assayable upon liberation, has been bound with the reducing terminal of maltooligosaccharide and the 4- and/or 6-position hydroxyl group of non-reducing terminal glucose have/has been modified, and the like may be used.

In the method using the reagent of the aforementioned (1) and (2), the adjuvant enzyme such as α-glucosidase, which has been added to lead the hydrolysate resulting from the amylase reaction into a detectable substance, acts to increase reaction of the blank. The method using the reagent of (3) theoretically enables to obviate the action of α-glucosidase and, therefore, is more preferable than the above methods which use a reagent of (1) and (2). In practice, however, a by-product, wherein the non-reducing terminal is not modified, is somewhat contained and a slight increase in the blank value is inevitable. The use of adjuvant enzyme also poses a problem of high cost. These problems similarly occur when a reagent and an antibody are combined for assaying isozyme.

Thus, (4) a method using 2chloro-4-nitrophenylmaltotrioside, which obviates the need of adjuvant enzyme, as a substrate has been developed (Japanese Patent Unexamined Publication No. 183595/1988), which circumvents the aforementioned problems in α-amylase activity assay. This method, nevertheless, has low sensitivity, and requires addition of thiocyanate or azide at a high concentration as an amylase activator. When this method and an antibody are combined to assay amylase isozyme (Clin. Chim. Acta., No. 259, pages 147–160, 1997), however, the high concentration activator prevents sufficient S-type amylase inhibitory activity. To avoid this, the activator content needs to be lowered to a certain level, which degrades the sensitivity of the method. Moreover, the addition of azide at a high concentration poses problems of possible toxicity and creation of an explosive compound upon bonding with a heavy metal.

SUMMARY OF THE INVENTION

The present invention therefore aims at providing a reagent for easy and precise assay of amylase isozyme activity, which contains a low concentration activator and an antibody inhibiting S-type amylase activity or P-type amylase activity but does not contain adjuvant enzyme, and assay methods using this reagent.

According to the present invention, there has been provided the use of 2-chloro-4-nitrophenyl 4-O-β-D-galactopyranosylmatoside as a substrate for amylase activity assay.

That is, the present invention provides a reagent for assaying amylase isozyme activity, which characteristically contains 2-chloro4-nitrophenyl 4-O-β-D-galactopyranosylmaltoside, an antibody inhibiting S-type amylase activity or P-type amylase activity, and an amylase activator.

The present invention also provides a method for assaying amylase isozyme activity, which comprises the steps of:
(a) bringing a reagent for amylase isozyme activity assay, which contains 2-chloro-4-nitrophenyl 4O-β-D-galactopyranosylmaltoside, an antibody having S-type amylase activity or P-type amylase activity-inhibitory activity, and an amylase activator, into contact with a sample containing P-type amylase and S-type amylase to allow reaction of 2-chloro-4-nitrophenyl 4-O-β-D-galactopyranosylmaltoside and the P-type amylase or S-type amylase, and
(b) assaying a content of liberated 2-chloro-4-nitrophenol.

Moreover, the present invention provides a method for assaying amylase isozyme activity, which comprises the steps of
(a) bringing a reagent for amylase isozyme activity assay, which contains 2-chloro-4-nitrophenyl 4-O-β-D-galactopyranosylmaltoside and an amylase activator, into contact with a sample containing P-type amylase and S-type amylase to allow reaction of 2-chloro-4nitrophenyl 4-O-β-D-galactopyranosylmaltoside and the P-type amylase and S-type amylase,
(b) assaying a content (A) of liberated 2-chloro-4-nitrophenol,
(c) bringing a reagent for amylase isozyme activity assay, which contains 2-chloro-4-nitrophenyl 4-O-β-D-galactopyranosylmaltoside, an antibody having S-type amylase activity or P-type amylase activity-inhibitory activity, and an amylase activator, into contact with a sample containing P-type amylase and S-type amylase to allow reaction of 2-chloro-4-nitrophenyl 4-O-βD-galactopyranosylmaltoside and the P-type amylase or S-type amylase,
(d) assaying a content (B) of liberated 2-chloro-4-nitrophenol, and
(e) subtracting the (B) from the (A).

DETAILED DESCRIPTION OF THE INVENTION

The sample containing amylase isozyme to be used in the present invention is not particularly limited and is exemplified by various body fluids, secretion, excretion and the like, such as blood (e.g., serum, plasma and the like), urine, saliva, pancreatic juice and the like.

The substrate to be used for the reagent for amylase isozyme activity assay of the present invention is 2-chloro-4-nitrophenyl 4-O-β-D-galactopyranosylmaltoside. This compound contains a galactopyranosyl group, which is a modifying group of the non-reducing terminal glucose, bonded to the 4-position hydroxyl group in β type. The reducing terminal is bonded with 2-chloro-4-nitrophenyl group as aglycon at 1-position hydroxyl group via α-glucoside linkage. This linkage is cleaved by α-amylase, and 2-chloro-4-nitrophenol produced upon cleavage of this bond becomes an assayable substance. This substrate can be produced by various known methods such as the method disclosed in Japanese Patent Unexamined Publication No. 264596/1991.

The final concentration of 2-chloro-4-nitrophenyl 4O-β-D-galactopyranosylmaltoside in the reagent is not particularly limited, but it is preferably 0.5–20 mM.

The antibody which inhibits S-type amylase activity and which is used for the reagent for amylase isozyme activity assay of the present invention is that which inhibits the reaction between S-type amylase and a substrate at high percentages by selectively binding with the S-type amylase, but which hardly inhibits the reaction between P-type amylase and a substrate. Similarly, the antibody which inhibits P-type amylase activity is that which inhibits the reaction between P-type amylase and a substrate at high percentages, but which hardly inhibits the reaction between S-type amylase and a substrate. While the percent inhibition of one of the amylase is isozyme activities, which is the target of each antibody, cannot be indiscriminately defined due to variation in conditions, such as production method of antibody and addition concentration, it is generally not less than 90%. Conversely, the percent inhibition of the other amylase isozyme activity is generally not more than 10%. When the above-mentioned property cannot be obtained with only one kind of an antibody, two or more kinds of antibodies may be concurrently used. When two or more kinds of antibodies are used, it is essential that the antibodies as a whole have an inhibitory action on each of the target amylase isozyme activities.

This antibody may be a polyclonal antibody or a monoclonal antibody.

These antibodies are prepared by various known methods. When preparing an antibody inhibiting S-type amylase activity, for example, a suitable test animal, such as mouse, is immunized with S-type amylase as an immunogen, and then the spleen cells of the test animal are fused with myeloma cells. The fused cells are grown on a culture dish or in ascites and screened to give a monoclonal antibody. Examples of the S-type amylase inhibitory antibody include commercially available 66C7 and 88E8 (Roche Diagnostics K.K.) and the like.

The antibody inhibiting P-type amylase activity can be prepared by a known method such as those mentioned above.

The final concentration of the antibody inhibiting S-type amylase activity in a reagent is not particularly limited, but it is preferably 5–100 mg/L.

Similarly, the final concentration of the antibody inhibiting P-type amylase activity in a reagent is not particularly limited, but it is preferably 5–100 mg/L.

The reagent for amylase is isozyme activity assay of the present invention contains thiocyanate and/or azide as an amylase activator to activate the reactivity of amylase. The final concentration is preferably 50–400 mM for thiocyanate and 1–90 mM for azide.

As compared to the concentration when using a conventional substrate, 2-chloro-4-nitrophenylmaltotrioside, these concentrations are low. For example, the concentration disclosed in Clin. Chim. Acta., No. 259 at page 147, line 5 is 450 mM for thiocyanate and that in Clin. Chem., Vol. 34, No. 10 at page 2007, right column, line 11 is 152 mM for azide.

Examples of thiocyanate include potassium thiocyanate, sodium thiocyanate and the like, and examples of azide include sodium azide and the like.

The reagent for amylase isozyme activity assay of the present invention contains surfactant, stabilizer, antiseptics, chelating agent and the like where necessary.

The reagent for the assay of the present invention may contain a buffer containing a dissolved substrate. Examples of the buffer include Good buffer such as MES buffer and the like, and various other buffers having buffering capability at around neutral range, such as phosphate buffer, Tris-HCl buffer and the like.

The reagent for amylase isozyme activity assay of the present invention does not need an adjuvant enzyme. The adjuvant enzyme means exo-glucosidase that hydrolyzes glucoside linkage from a non-reducing terminal, which is exemplified by α-glucosidase, β-glucosidase, glucoamylase and the like.

The amylase isozyme activity assay method using the reagent for amylase isozyme activity assay of the present invention comprises the steps of:

(1) bringing a reagent for amylase isozyme activity assay, which contains 2-chloro-4-nitrophenyl 4-O-β-D-galactopyranosylmaltoside, an antibody having S-type amylase activity or P-type amylase activity-inhibitory activity, and an amylase activator, into contact with a sample containing P-type amylase and S-type amylase to allow reaction of 2-chloro-4-nitrophenyl 4-O-β-D-galactopyranosylmatoside and the P-type amylase or S-type amylase, and (2) assaying the content of liberated 2-chloro-4-nitrophenol.

By these steps, one of the P-type amylase and S-type amylase, which reacted with the above-mentioned maltooligosaccharide derivative, can be assayed for the amylase isozyme activity. Further, the amylase isozyme activity of the other amylase that could not be assayed by the above steps can be determined by assaying the total activity of S-type amylase and P-type amylase using a reagent without antibody and subtracting the isozyme activity of the amylase assayed by the above steps.

The reaction between 2-chloro-4-nitrophenyl 4-O-β-D-galactopyranosylmaltoside and each amylase isozyme proceeds, for example, at a reaction temperature of 25–40° C., pH 5–8 for about 1–20 minutes. The reaction between the substrate and the P-type amylase and S-type amylase proceeds in the same manner.

The reaction formulas of substrate decomposition in the present invention are shown below.

2-chloro-4-nitrophenyl 4-O-β-D-galactopyranosylmaltoside

P-type amylase or S-type amylase (one of the amylase isozymes does
not react due to the action of inhibitory antibody)
amylase activator (thiocyanate and/or azide)

2-chloro-4-nitrophenol and

4-O-β-D-galactoanosylmaltose

The 2-chloro-4-nitrophenol liberated by the above reaction is assayed by a suitable method for determining the activity of each amylase isozyme. For example, since 2-chloro-4-nitrophenol shows absorbance at around 400 nm, the changes in absorbance at around 400 nm are measured after liberation.

The method for assaying 2-chloro-4-nitrophenol may be a rate method wherein the reaction of amylase is continuously monitored or an endpoint method wherein a reaction is carried out for a certain time and terminated for assay.

The present invention is explained in more detail in the following by way of Examples, to which the present invention is not limited.

EXAMPLE 1 and

Comparative Example 1

A reagent for amylase isozyme activity assay comprising each composition as mentioned below was prepared. In the Table showing the composition, GalG2CNP (Example) is 2-chloro-4-nitrophenyl 4-O-β-D-galactopyranosylmaltoside, and G3CNP (Comparative Example) is 2-chloro-4-nitrophenylmaltotrioside.

1. Reagent Compositions
(1) Composition A
   Good buffer (pH 6.0) 50 mM
   Sodium chloride 300 mM
   Calcium chloride 5 mM
   S-type amylase-inhibiting antibody 88E8 (manufactured by Roche Diagnostics K.K.) 20 mg/L
   S-type amylase-inhibiting antibody 66C7 (manufactured by Roche Diagnostics K.K.) 5 mg/L
   Potassium thiocyanate 900 to 0 mM (concentrations are shown in Tables 1 and 2)
   Substrate (GalG2CNP (Example) or G3CNP (Comparative Example)) 2.6 mM
(2) Composition B
   Good buffer (pH 6.0) 50 mM
   Sodium chloride 300 mM
   Calcium chloride 5 mM
   Potassium thiocyanate 900 to 0 mM (concentrations are shown in Tables 1 and 2)
   Substrate (GalG2CNP (Example) or G3CNP (Comparative Example)) 2.6 mM
2. Samples
(1) Distilled Water
(2) P-type Amylase (Calibzyme P, Manufactured by International Reagents Corporation)
(3) S-type Amylase (Calibzyme S, Manufactured by International Reagents Corporation)

Each sample (0.05 mL was added to the reagent A (3 mL) and the reagent B (3 mL), respectively, and the mixtures were allowed to stand at 37° C. for 3 minutes. Then, the change in absorbance at 405 nm was assayed, and the change in absorbance per minute was calculated. The results are shown in Tables 1 and 2.

In the Tables, P is the case where P-type amylase was used as the sample, and S is the case where S-type amylase was used. The relative sensitivity of P and S is based on the change in absorbance of G3CNP as 100, wherein potassium thiocyanate had a concentration of 900 mM.

Percent residual enzyme activity and relative sensitivity were calculated by the following formulas, wherein the percent residual enzyme activity shows the proportion of each amylase isozyme which was not inhibited by antibody and the reciprocal thereof is the percent inhibition of each amylase isozyme by the antibody.

Percent residual enzyme activity (%)=(change in absorbance of composition A)/(change in absorbance of composition B)×100

Relative sensitivity (%)=(change in absorbance of composition B)/(change in absorbance of Comparative Example wherein potassium thiocyanate was 900 mM)×100

TABLE 1

GalG2CNP (Example)

| | Final concentration of potassium thiocyanate (mM) | Containing Antibody (Composition A) (mABS/min) | Without antibody (Composition B) (mABS/min) | Percent residual enzyme activity (%) | Relative sensitivity (%) |
|---|---|---|---|---|---|
| P | 900 | 61.6 | 60.1 | 102.5 | 125.5 |
| | 800 | 63.7 | 62.6 | 101.8 | 130.7 |
| | 700 | 67.9 | 67.2 | 101.0 | 140.3 |
| | 600 | 70.4 | 68.0 | 103.5 | 142.0 |
| | 500 | 71.3 | 70.9 | 100.6 | 148.0 |
| | 400 | 70.3 | 71.7 | 98.0 | 149.7 |
| | 300 | 66.6 | 69.1 | 96.4 | 144.3 |
| | 200 | 59.5 | 61.9 | 96.1 | 129.2 |
| | 140 | 52.4 | 56.0 | 93.6 | 116.9 |
| | 100 | 49.3 | 51.1 | 96.5 | 106.7 |
| | 50 | 40.6 | 42.1 | 96.4 | 87.9 |
| | 0 | 26.2 | 26.7 | 98.1 | 55.7 |
| S | 900 | 9.6 | 43.3 | 22.2 | 96.9 |
| | 800 | 8.2 | 47.1 | 17.4 | 105.4 |
| | 700 | 7.2 | 48.6 | 14.8 | 108.7 |
| | 600 | 5.7 | 51.9 | 11.0 | 116.1 |
| | 500 | 4.7 | 53.7 | 8.8 | 120.1 |
| | 400 | 3.8 | 54.5 | 7.0 | 121.9 |
| | 300 | 3.0 | 53.6 | 5.6 | 119.9 |
| | 200 | 2.2 | 50.0 | 4.4 | 111.9 |
| | 140 | 1.8 | 44.6 | 4.0 | 99.8 |
| | 100 | 1.7 | 40.2 | 4.2 | 89.9 |
| | 50 | 1.4 | 31.1 | 4.5 | 69.6 |
| | 0 | 0.9 | 14.3 | 6.3 | 32.0 |

TABLE 2

G3CNP (Comparative Example)

| | Final concentration of potassium thiocyanate (mM) | Containing Antibody (Composition A) (mABS/min) | Without antibody (Composition B) (mABS/min) | Percent residual enzyme activity (%) | Relative sensitivity (%) |
|---|---|---|---|---|---|
| P | 900 | 48.6 | 47.9 | 101.5 | 100.0 |
| | 800 | 49.8 | 48.8 | 102.0 | 101.9 |
| | 700 | 49.9 | 49.4 | 101.0 | 103.1 |
| | 600 | 48.1 | 47.5 | 101.3 | 99.2 |
| | 500 | 46.6 | 46.7 | 99.8 | 97.5 |
| | 400 | 42.6 | 43.7 | 97.5 | 91.2 |
| | 300 | 37.3 | 39.3 | 94.9 | 82.0 |
| | 200 | 30.3 | 31.6 | 95.9 | 66.0 |
| | 140 | 26.1 | 27.2 | 96.0 | 56.8 |
| | 100 | 22.3 | 23.4 | 95.3 | 48.9 |
| | 50 | 17.1 | 17.7 | 96.6 | 37.0 |
| | 0 | 9.3 | 9.3 | 100.0 | 19.4 |
| S | 900 | 10.0 | 44.7 | 22.4 | 100.0 |
| | 800 | 8.4 | 45.8 | 18.3 | 102.5 |
| | 700 | 7.0 | 47.1 | 14.9 | 105.4 |
| | 600 | 5.4 | 47.3 | 11.4 | 105.8 |
| | 500 | 4.6 | 45.8 | 10.0 | 102.5 |
| | 400 | 3.3 | 43.2 | 7.6 | 96.6 |
| | 300 | 2.2 | 39.7 | 5.5 | 88.8 |
| | 200 | 1.5 | 31.4 | 4.8 | 70.2 |
| | 140 | 1.3 | 26.6 | 4.9 | 59.5 |
| | 100 | 0.9 | 21.9 | 4.1 | 49.0 |
| | 50 | 0.7 | 14.8 | 4.7 | 33.1 |
| | 0 | 0.5 | 4.9 | 10.2 | 11.0 |

Figure 1:
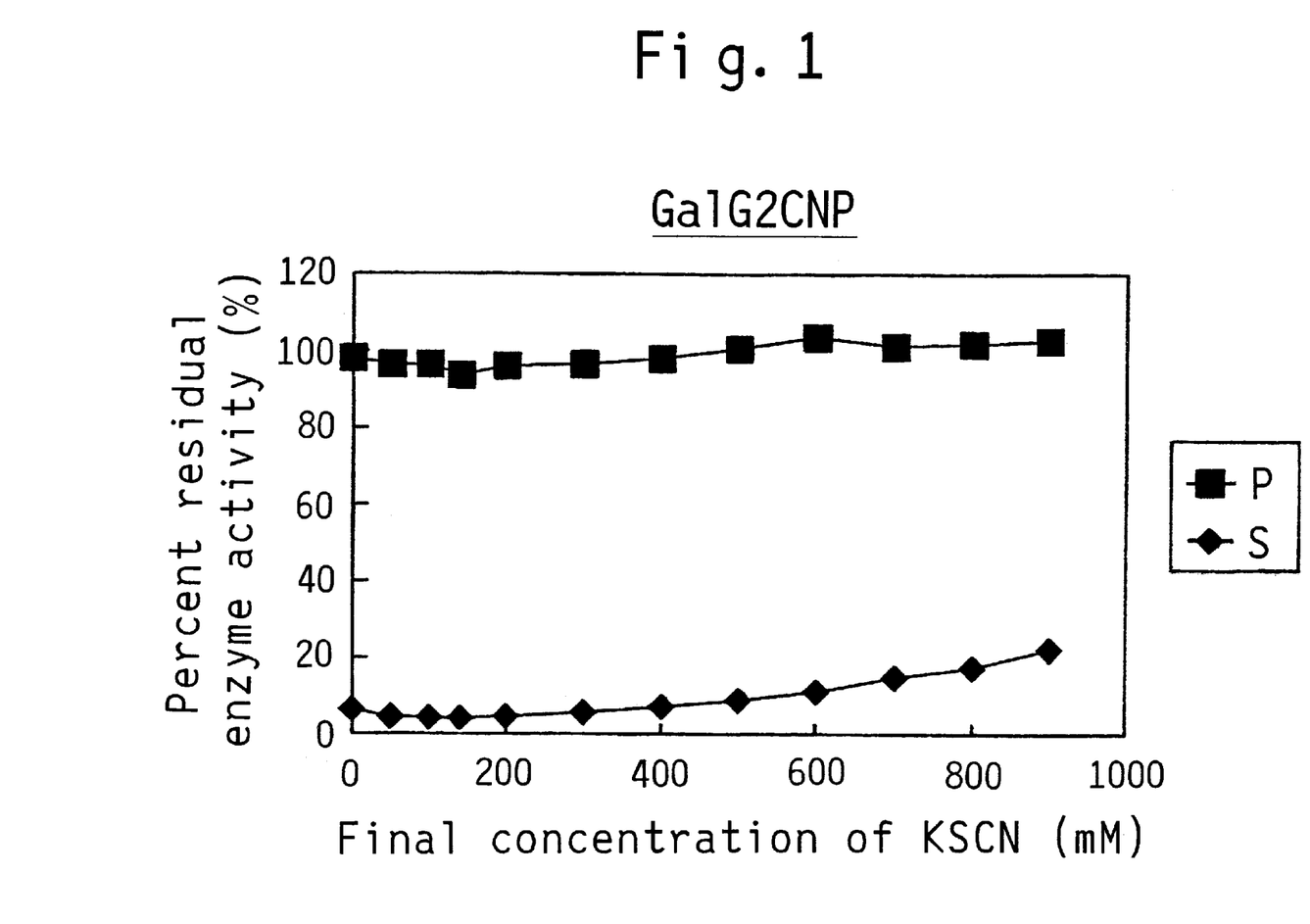
FIG. 1 shows the relationship between potassium thiocyanate concentration and percent inhibition of each isozyme activity when the substrate (GalG2CNP) of the present invention was used.
Figure 2:
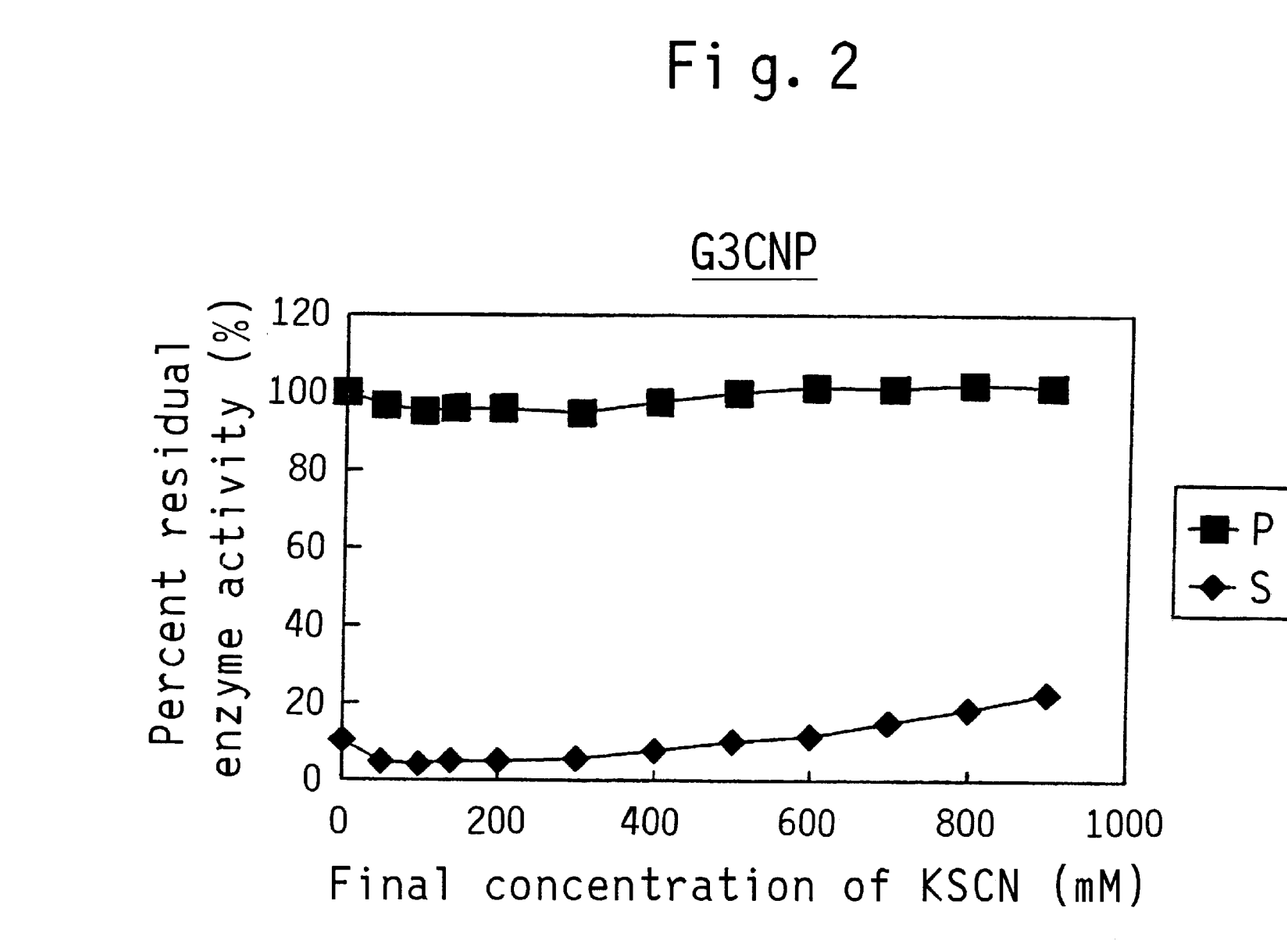
FIG. 2 shows the relationship between potassium thiocyanate concentration and percent inhibition of each isozyme activity when the substrate (G3CNP) of the Comparative Example was used.

Using the results of Tables 1 and 2, the relationship between the concentration of potassium thiocyanate of each substrate and the percent inhibition of each isozyme is shown in FIG. 1 (Example) and FIG. 2 (Comparative Example).

Figure 3:
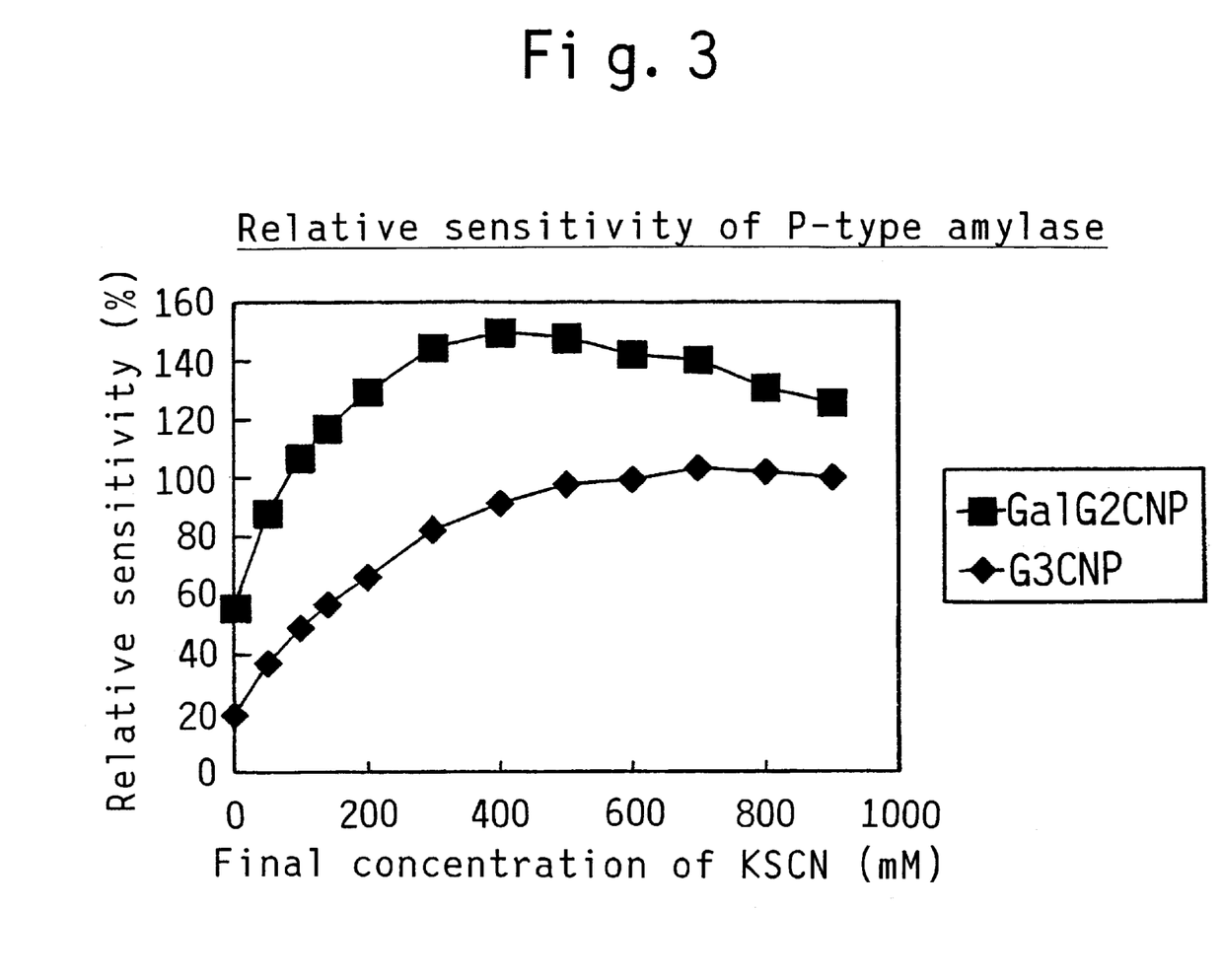
FIG. 3 shows the relationship between potassium thiocyanate concentration and change in absorbance per minute during P-type amylase assay when the substrate (GalG2CNP) of the present invention and the substrate (G3CNP) of the Comparative Example were used.

In addition, the relationship between the concentration of potassium thiocyanate and change in absorbance per minute during P-type amylase assay is shown in FIG. 3.

According to FIG. 1 and FIG. 2, the percent inhibition of S-type amylase became lower with higher potassium thiocyanate concentrations in both Example 1 and Comparative Example 1, and at 600 mM it was not more than 90% and at 900 mM, it was not more than 80%, wherein the percent inhibition exceeded 95% in Example and Comparative Example only in the range of 50–200 mM. According to FIG. 3, the relative sensitivity of P-type amylase in Comparative Example 1 started decreasing at a potassium thiocyanate concentration of not more than 500 mM, and at 200 mM, it became about ⅔ of the standard sensitivity (which is the sensitivity when potassium thiocyanate concentration is 900 mM using 2-chloro-4-nitrophenylmaltotrioside and which is taken as 100%). In the case of Example 1, the relative sensitivity at a potassium thiocyanate concentration of 200 mM was about 1.3 times as great as the standard sensitivity, thus showing higher sensitivity of Example 1.

EXAMPLE 2
and
Comparative Example 2

Reagents for amylase isozyme activity assay having the following compositions were respectively prepared.

1. Reagent Compositions
(1) Composition C
  Good buffer (pH 6.0) 50 mM
  Sodium chloride 300 mM
  Calcium chloride 5 mM
  S-type amylase inhibitory antibody 88E8 (manufactured by Roche Diagnostics K.K.) 20 mg/L
  S-type amylase inhibitory antibody 66C7 (manufactured by Roche Diagnostics K.K.) 5 mg/L Sodium azide 300 to 0 mM (concentrations are shown in Tables 3 and 4)

Substrate (GalG2CNP (Example) or G3CNP (Comparative Example)) 2.6 mM (2) Composition D Good buffer (H 6.0) 50 mM Sodium chloride 300 mM Calcium chloride 5 mM Sodium azide 300 to 0 mM (concentrations are shown in Tables 3 and 4)

Substrate (GalG2CNP (Example) or G3CNP (Comparative Example)) 2.6 mM

2. Samples (1) Distilled Water (2) P-type Amylase (Calibzyme P, Manufactured by International Reagents Corporation)

(3) S-type Amylase (Calibzyme S, Manufactured by International Reagents Corporation)

Each of the above-mentioned samples (0.05 mL) was added to respective reagent C and D (3 mL) and the mixtures were left standing at 37° C. for 3 minutes. Then, change in absorbance at 405 nm was assayed and change in absorbance per minute was calculated.

The results are shown in Tables 3 and 4.

In the Tables, P is the case where P-type amylase was used as the sample, and S is the case where S-type amylase was used. The relative sensitivity of P and S is based on the change in absorbance of G3CNP as 100, wherein sodium azide was 300 mM.

Percent residual enzyme activity and relative sensitivity were calculated by the following formulas.

Percent residual enzyme activity (%)=(change in absorbance of composition C)/(change in absorbance of composition D)×100

Relative sensitivity (%)=(change in absorbance of composition D)/(change in absorbance of Comparative Example wherein sodium azide was 300 mM)×100

TABLE 3

GalG2CNP (Example)

| Final concentration of sodium azide (mM) | | Containing Antibody (Composition C) (mABS/min) | Without antibody (Composition D) (mABS/min) | Percent residual enzyme activity (%) | Relative sensitivity (%) |
|---|---|---|---|---|---|
| P | 300 | 76.8 | 75.6 | 101.6 | 165.8 |
|   | 250 | 74.4 | 72.4 | 102.8 | 158.8 |
|   | 200 | 72.2 | 70.1 | 103.0 | 153.7 |
|   | 150 | 68.2 | 68.4 | 99.7 | 150.0 |
|   | 120 | 64.9 | 63.4 | 102.4 | 139.0 |
|   | 90 | 60.1 | 59.6 | 100.8 | 130.7 |
|   | 60 | 52.5 | 52.8 | 99.4 | 115.8 |
|   | 30 | 43.6 | 44.6 | 97.8 | 97.8 |
|   | 0 | 26.4 | 26.3 | 100.4 | 57.7 |
| S | 300 | 2.6 | 66.8 | 3.9 | 145.5 |
|   | 250 | 2.5 | 67.3 | 3.7 | 146.6 |
|   | 200 | 2.6 | 61.1 | 4.3 | 133.1 |
|   | 150 | 2.4 | 57.8 | 4.2 | 125.9 |
|   | 120 | 2.6 | 53.1 | 4.9 | 115.7 |
|   | 90 | 2.4 | 49.6 | 4.8 | 108.1 |
|   | 60 | 2.0 | 43.8 | 4.6 | 95.4 |
|   | 30 | 1.6 | 33.2 | 4.8 | 72.3 |
|   | 0 | 0.8 | 14.6 | 5.5 | 31.8 |

TABLE 4

G3CNP (Comparative Example)

| Final concentration of sodium azide (mM) | | Containing Antibody (Composition C) (mABS/min) | Without antibody (Composition D) (mABS/min) | Percent residual enzyme activity (%) | Relative sensitivity (%) |
|---|---|---|---|---|---|
| P | 300 | 45.4 | 45.6 | 99.6 | 100.0 |
|   | 250 | 43.6 | 42.8 | 101.9 | 93.9 |
|   | 200 | 40.9 | 41.3 | 99.0 | 90.6 |
|   | 150 | 37.5 | 37.1 | 101.1 | 81.4 |
|   | 120 | 35.3 | 33.7 | 104.7 | 73.9 |
|   | 90 | 31.8 | 32.0 | 99.4 | 70.2 |
|   | 60 | 26.3 | 26.0 | 101.2 | 57.0 |
|   | 30 | 19.8 | 20.5 | 96.6 | 45.0 |
|   | 0 | 9.4 | 9.4 | 100.0 | 20.6 |
| S | 300 | 2.3 | 45.9 | 5.0 | 100.0 |
|   | 250 | 2.2 | 44.5 | 4.9 | 96.9 |
|   | 200 | 1.9 | 41.1 | 4.6 | 89.5 |
|   | 150 | 1.6 | 35.8 | 4.5 | 78.0 |
|   | 120 | 1.5 | 31.0 | 4.8 | 67.5 |
|   | 90 | 1.6 | 28.6 | 5.6 | 62.3 |
|   | 60 | 1.0 | 22.4 | 4.5 | 48.8 |
|   | 30 | 0.9 | 15.7 | 5.7 | 34.2 |
|   | 0 | 0.3 | 4.7 | 6.4 | 10.2 |

Figure 4:
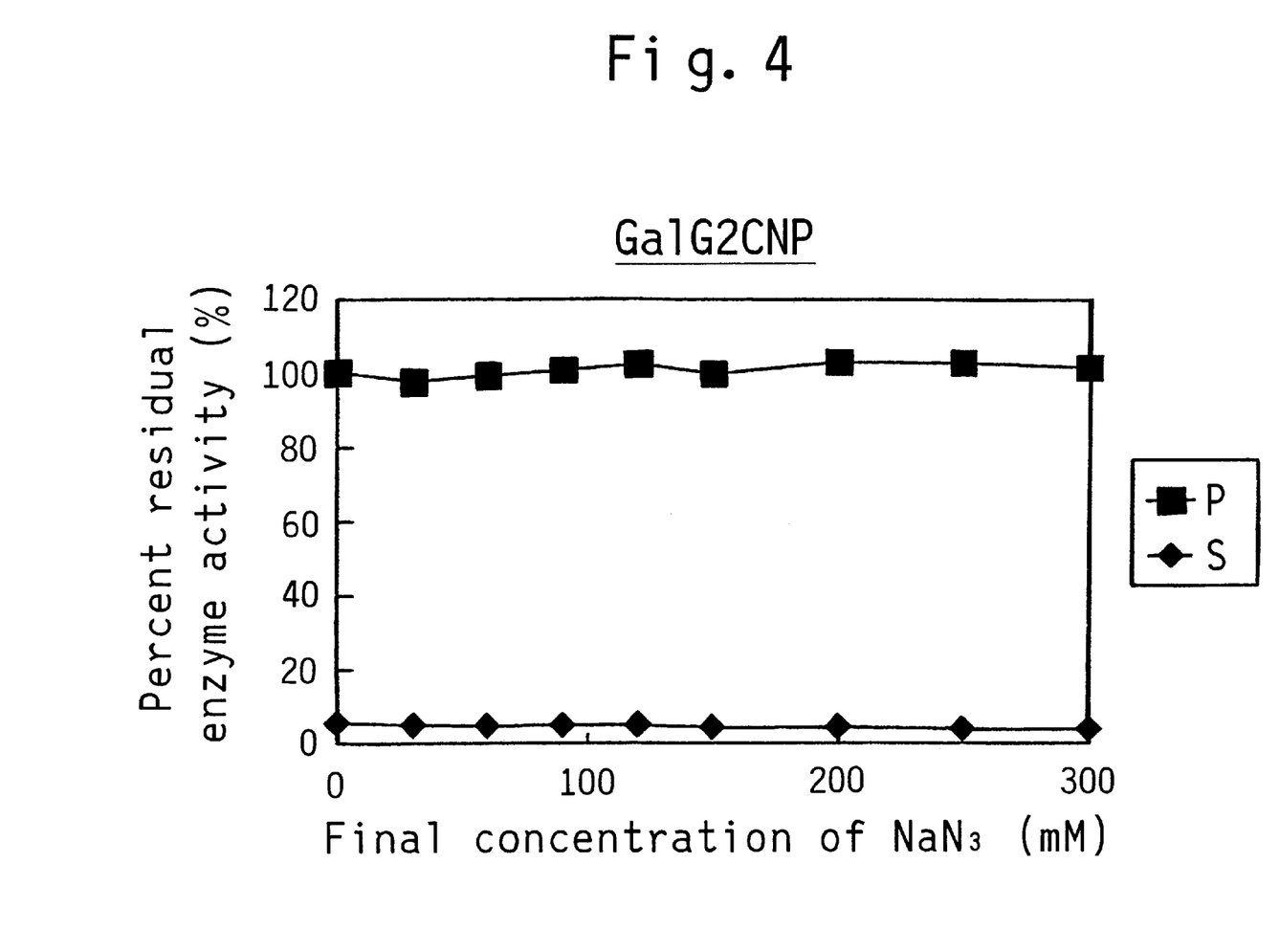
FIG. 4 shows the relationship between sodium azide and percent inhibition of each isozyme activity when the substrate (GalG2CNP) of the present invention was used.
Figure 5:
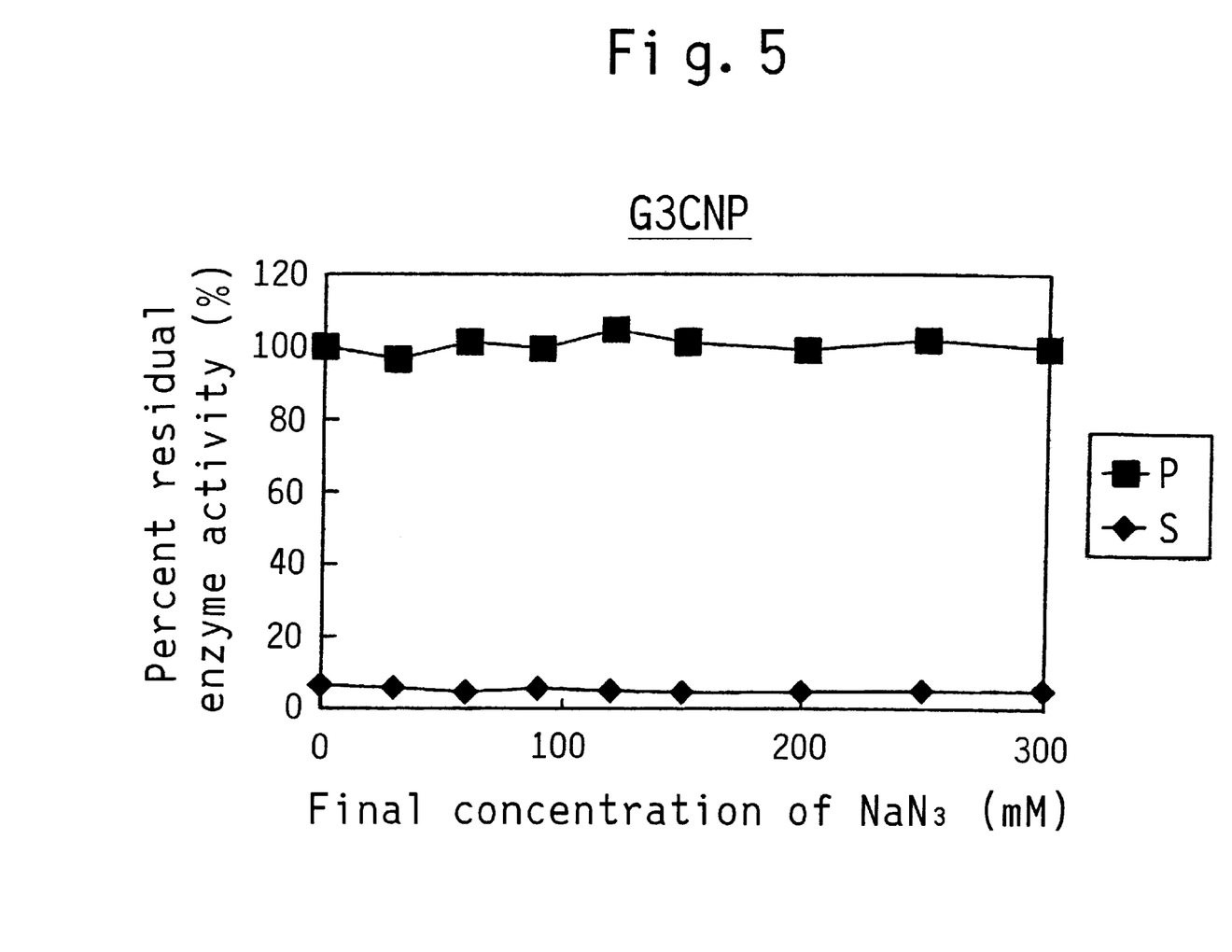
FIG. 5 shows the relationship between sodium azide and percent inhibition of each isozyme activity when the substrate (G3CNP) of Comparative Example was used.
Figure 6:
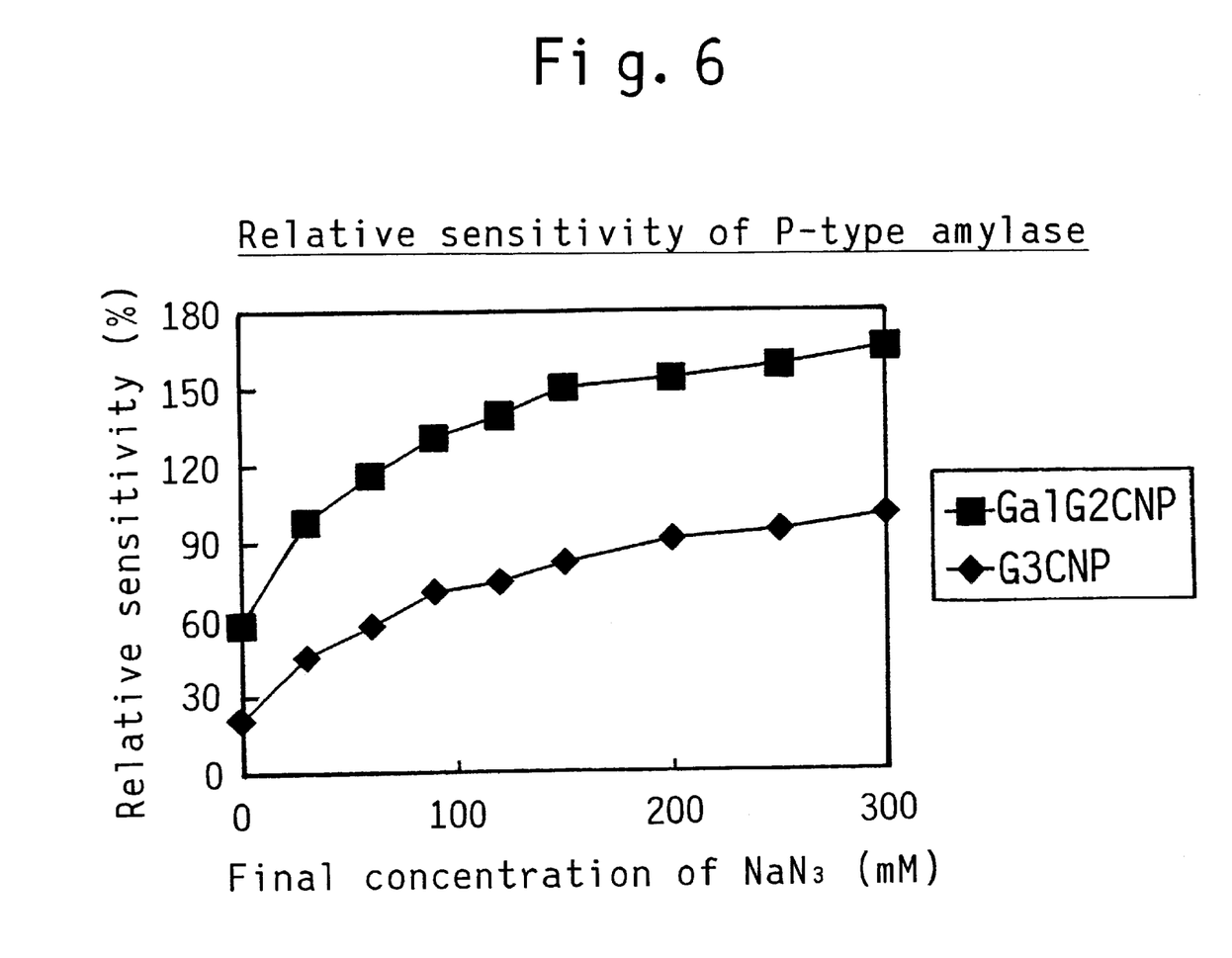
FIG. 6 shows the relationship between sodium azide concentration and change in absorbance per minute during P-type amylase assay when the substrate (GalG2CNP) of the present invention and the substrate (G3CNP) of the Comparative Example were used.

Using the results of Tables 3 and 4, the relationship between the concentration of sodium azide of each substrate and the percent inhibition of each isozyme shown in FIG. 4 and FIG. 5. In addition, the relationship between the concentration of sodium azide and change in absorbance per minute during P-type amylase assay is shown in FIG. 6.

According to FIG. 4 and FIG. 5, the percent inhibition of S-type amylase was around 95% irrespective of sodium azide concentrations in both Example 2 and Comparative Example 2. According to FIG. 6, moreover, the relative sensitivity of P-type amylase in Comparative Example 2 decreased with lower sodium azide concentrations. At 30 mM, it became about 45% of the standard sensitivity (which is the sensitivity when sodium azide concentration is 300 mM using 2-chloro-4-nitrophenylmaltotrioside and which is taken as 100%). In the case of Example, the relative sensitivity at a sodium azide concentration of 30 mM was about 98% of the standard sensitivity, thus indicating that the concentration of the added sodium azide necessary for achieving the sensitivity similar to that in Comparative Example is lower in Example.

EXAMPLE 3 and

Comparative Example 3

The reagents having the following compositions were prepared.

1. Reagent compositions (1) Composition E

Good buffer (pH 6.2) 50 mM

Sodium chloride 300 mM

Calcium chloride 5 mM

S-type amylase inhibitory antibody 88E8 (manufactured by Roche Diagnostics K.K.) 15 mg/L S-type amylase inhibitory antibody 66C7 (manufactured by Roche Diagnostics K.K.) 1.25 mg/L Potassium thiocyanate 140 mM Substrate (GalG2CNP (Example) or G3CNP (Comparative Example)) 2.6 mM 2. Samples
   (1) Distilled water (blank)
   (2) Serum (1, 2 or 3)
3. Assay Each of the above-mentioned reagents (0.05 mL) was added to the above reagent E (3 mL) and the mixtures were left standing at 37° C. for 3 minutes. Then, change in absorbance at 405 nm was assayed and change in absorbance per minute was calculated. The obtained change in absorbance was converted to P-type amylase activity value at this composition using the molecular extinction coefficient of CNP. The results are shown in Table 5.

According to Table 5, the assay using the reagent of Example (substrate is GalG2CNP) showed greater change in absorbance than in the assay in Comparative Example (substrate was G3CNP), thus indicating superior sensitivity.

TABLe 5

|  | Serum 1 | Serum 2 | Serum 3 | Blank |
| --- | --- | --- | --- | --- |
| Example | 32.3 | 205.0 | 156.8 | 0.0004 |
| Comparative Example | 16.8 | 106.3 | 80.9 | 0.0006 |
|  | (IU/L) | (IU/L) | (IU/L) | (ABS/min) |

EXAMPLE 4
and

Comparative Example 4

The reagents having the following compositions were prepared.
1. Reagent Compositions
   (1) Composition F
      Good buffer (pH 6.2) 50 mM
      Sodium chloride 300 mM
      Calcium chloride 5 mM
      Potassium thiocyanate 140 mM
      Substrate (GalG2CNP (Example) or G3CNP (Comparative Example)) 2.6 mM
   (2) Composition G
      Good buffer (pH 6.2) 50 mM
      Sodium chloride 300 mM
      Calcium chloride 5 mM
      Potassium thiocyanate 140 mM
      S-type amylase inhibitory antibody 88E8 (manufactured by Roche Diagnostics K.K.) 15 mg/L
      S-type amylase inhibitory antibody 66C7 (manufactured by Roche Diagnostics K.K.) 1.25 mg/L
      Substrate (GalG2CNP (Example) or G3CNP (Comparative Example)) 2.6 mM
2. Samples
   (1) Distilled Water(Blank)
   (2) Serum (1, 2 or 3)
3. Assay Each of the above-mentioned reagents (0.05 mL) was added to the above reagent F (3 mL) and the mixtures were left standing at 37° C. for 3 minutes. Then, change in absorbance at 405 nm was assayed and change in absorbance per minute was calculated (change in absorbance a). The same procedure was repeated using reagent G and change in absorbance per minute was calculated (change in absorbance b). Then, change in absorbance b was subtracted from change in absorbance a to give change in absorbance c, which was converted to S-type amylase activity value at this composition using the molecular extinction coefficient of CNP. The results are shown in Table 6.

According to Table 6, the assay using the reagent of Example (substrate is GalG2CNP) showed greater change in absorbance than in the assay in Comparative Example (substrate is G3CNP), thus indicating superior sensitivity.

TABLE 6

|  | Serum 1 | Serum 2 | Serum 3 | Blank |
| --- | --- | --- | --- | --- |
| Example | 44.8 | 167.7 | 140.7 | 0.0003 |
| Comparative Example | 23.4 | 87.5 | 71.9 | 0.0006 |
|  | (IU/L) | (IU/L) | (IU/L) | (ABS/min) |

Using the reagent for amylase isozyme activity assay of the present invention containing a low concentration activator and an antibody having S-type amylase or P-type amylase activity inhibitory action but not containing an adjuvant enzyme, amylase isozyme activity can be assayed accurately and easily.

This application is based on application Nos. 37583/1998 and 23804/1999 filed in Japan, the contents of which are incorporated hereinto by reference. All publications are herein incorporated by reference to the same extent as if each individual publication was specifically described herein.

What is claimed is:

1. A reagent for amylase isozyme activity assay, which comprises 2-chloro-4-nitrophenyl 4-O-β-D-galactopyranosylmaltoside, an antibody inhibiting S-type amylase activity or P-type amylase activity, and thiocyanate as an amylase activator.

2. The reagent of claim 1, wherein the antibody inhibits S-type amylase activity.

3. The reagent of claim 2, wherein the antibody that inhibits S-type amylase activity has a final concentration of 5–100 mg/L and the 2-chloro-4-nitrophenyl 4-O-β-D-galactopyranosylmaltoside has a final concentration of 0.5–20 mM.

4. The reagent of claim 1, wherein the antibody inhibits P-type amylase activity.

5. The reagent of claim 4, wherein the antibody that inhibits P-type amylase activity has a final concentration of 5–100 mg/L and the 2-chloro-4-nitrophenyl 4-O-β-D-galactopyranosylmaltoside has a final concentration of 0.5–20 mM.

6. The reagent of claim 1, wherein the thiocyanate has a final concentration of 50–400 mM.

7. A method for detecting or measuring amylase isozyme activity, which comprises the steps of:
   a) bringing a reagent for amylase isozyme activity assay, which comprises 2-chloro-4-nitrophenyl 4-O-β-D-galactopyranosylmaltoside, an antibody having S-type amylase activity or P-type amylase activity-inhibitory activity, and thiocyanate, into contact with a sample containing P-type amylase and S-type amylase to allow reaction of 2-chloro-4-nitrophenyl 4-O-β-D-galactopyranosylmaltoside and the P-type amylase or S-type amylase, and
   b) determining the presence or amount of 2-chloro-4-nitrophenol liberated from 2-chloro-4-nitrophenyl 4-O-β-D-galactopyranosylmaltoside, indicating the activity of α amylase isozyme.

8. The method of claim 7, wherein in step(a), the antibody inhibits S-type amylase activity.

9. The method of claim 7, wherein in step(a), the antibody inhibits P-type amylase activity.

10. A method for detecting or measuring amylase isozyme activity, which comprises the steps of:
   a) bringing a reagent for amylase isozyme activity assay, which comprises 2-chloro-4-nitrophenyl 4-O-β-D-galactopyranosylmaltoside and thiocyanate, into contact with an aliquot of a sample containing P-type amylase and S-type amylase to allow reaction of 2-chloro-4-nitrophenyl 4-O-β-D-galactopyranosylmaltoside and the P-type amylase and S-type amylase, and
   b) determining the presence or amount (A) of 2-chloro-4-nitrophenol liberated from 2-chloro-4-nitrophenyl 4-O-β-D-galactopyranosylmaltoside, indicating the activity of α amylase present in the sample,
   c) bringing a reagent for amylase isozyme activity assay, which comprises 2-chloro-4-nitrophenyl 4-O-β-D-galactopyranosylmaltoside, an antibody having S-type amylase activity or P-type amylase activity-inhibitory activity, and thiocyanate, into contact with an aliquot of the sample containing P-type amylase and S-type amylase to allow reaction of 2-chloro-4-nitrophenyl 4-O-β-D-galactopyranosylmaltoside and the P-type amylase or S-type amylase,
   d) determining the presence or amount (B) of 2-chloro-4-nitrophenol liberated from 2-chloro-4-nitrophenyl 4-O-β-D-galactopyranosylmaltoside, indicating the activity of α amylase isozyme S-type or P-Type, and
   e) subtracting the (B) from the (A).

11. The method of claim 10 wherein in step(c), the antibody inhibits S-type amylase activity.

12. The method of claim 10, wherein in step (c), the antibody inhibits P-type amylase activity.

\* \* \* \* \*